United States Patent [19]

Williams

[11] Patent Number: 5,179,957
[45] Date of Patent: Jan. 19, 1993

[54] BLOOD PRESSURE CUFF AND HOSE FITTING THEREFOR

[75] Inventor: Michael Williams, Coventry, Conn.

[73] Assignee: CAS Medical Systems, Inc., Branford, Conn.

[21] Appl. No.: 625,816

[22] Filed: Dec. 11, 1990

[51] Int. Cl.⁵ .............................................. A61B 5/022
[52] U.S. Cl. ..................................... 128/686; 606/202
[58] Field of Search ............... 128/677, 686, DIG. 20; 606/202

[56] References Cited

U.S. PATENT DOCUMENTS 3,603,304  9/1971  Maier ................................. 128/686

*Primary Examiner*—Lee S. Cohen
*Assistant Examiner*—Kevin Pontius
*Attorney, Agent, or Firm*—William W. Jones

[57] ABSTRACT

A polyurethane coated nylon sheet is folded medially to form the pressure cuff. The urethane coated surface forms the inner surface of the inflation chamber of the cuff. A hook and loop fastener assembly for securing the cuff about the patient's limb is secured to the cuff. The hook and loop sheets are both provided with fusable polymer back coatings. The hook and loop sheets are fused to the polyurethane coated surfaces on the cuff. The hooks and loops are accessible on opposite sides of the cuff. An inflation fitting is also fused to the interior of the pressure chamber and projects through an opening in the cuff.

4 Claims, 1 Drawing Sheet

BLOOD PRESSURE CUFF AND HOSE FITTING THEREFOR

This invention relates to an improved blood pressure cuff having a novel inflation hose fitting.

Blood pressure cuffs may be used with manually operated inflation and pressure detection paraphernalia, or with automatic instruments which inflate, deflate and read pressure values. Some cuffs use only a single inflation/deflation hose, and thus have only a single inflation hose fitting. Other cuffs are used with two hoses. The latter cuffs must thus have a dual capacity hose fitting, which requires two tubular components which connect to the two hoses. The hose fittings are now typically formed as single fitting units which are ganged in pairs when an automatic instrument cuff is being assembled. It would be desirable to provide a fitting that which could be used with either type cuff. The fitting must be compatible with either cuff type, and must be capable of sealing the inflation chamber in the cuff.

This invention relates to an improved blood pressure cuff which has a heat fusable polymeric inflation fitting component bonded to the cuff by means of a heat fusable polymeric coating on the interior of the cuff. The cuff is made from a fabric tube, such an nylon which is folded from a single sheet preform about a mid axial line to form the tube. The surface of the preform sheet which is brought into face-to-face contact with itself when the tube is formed is coated with a layer of a polymer such as polyurethane which renders the fabric impermeable to air, and which provides a heat activated fusable layer on the interior of the tube. The edges of the tube can thus be fused together to form the inflatable bladder in the cuff. The polymeric inflation fitting includes a flange part and one or two tubular parts for connection to inflation and sensor hoses. Die cut openings are made in the sheet preform at appropriate locations for receiving the tubular part or parts of the fitting. The polymer flange of the fitting is juxtaposed to the polymer surface of the sheet preform, whereupon the fitting is fused to the preform. The opening or openings are thus sealed with the fitting flange and the polymer tubular parts of the fitting are accessible through the openings from the exterior of the cuff for connection to air inflation and sensor tubes.

The fitting of this invention is molded with two tubular parts and a single flange encircling the tubular parts. In its molded form, the fitting can be used on cuffs which are used with two hoses. In case a single hose cuff is being produced, the two tubular parts can be separated from each other, and each separated tubular part will still have its own encircling flange for fusing to the cuff, which in that case will only have one fitting hole cut in it. Separation of the fitting components from each other can be accomplished easily when the cuff is being formed.

It is, thereofore, an object of this invention to provide an improved blood pressure cuff which employs a hose fitting for securement to hoses connected to the cuff.

It is a further object of this invention to provide an improved blood pressure cuff of the character described which has an internal polymeric coating and wherein the fitting has a basal flange formed from the same polymer.

It is another object of this invention to provide an improved blood pressure cuff of the character described wherein the fitting has two tubular portions joined by the basal flange.

It is an additional object of this invention to provide an improved blood pressure cuff of the character described wherein the duo-tubular fitting can be easily separated into two separate fittings each of which includes a basal flange.

These and other objects and advantages of the invention will become more readily apparent to those skilled in the art from the following detailed description of a preferred embodiment of the invention, when taken in conjunction with the accompanying drawings, in which.

Figure 1:
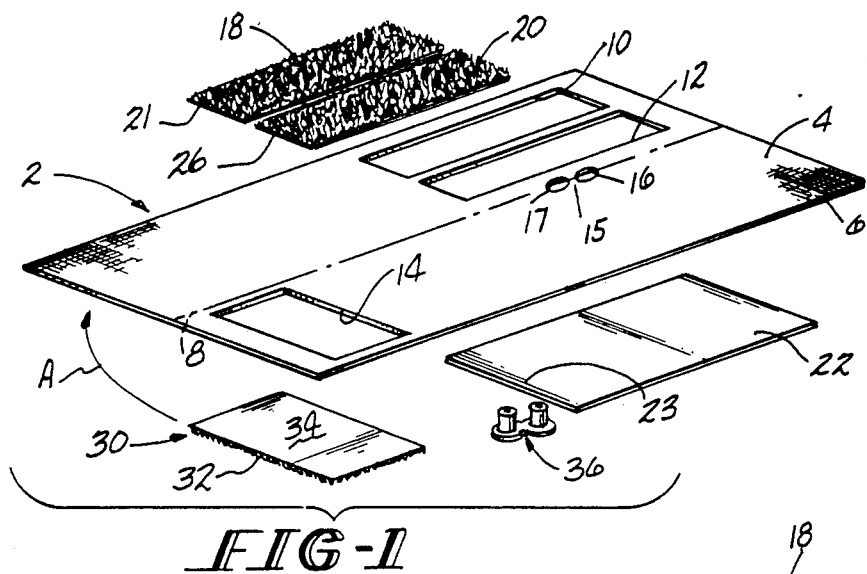
FIG. 1 is an exploded view of the blood pressure cuff of this invention in the preform stage.
Figure 2:
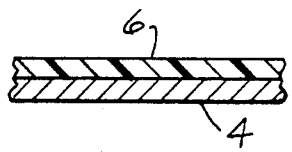
FIG. 2 is a cross sectional view of the coated fabric used to form certain parts of the cuff of FIG. 1.

Referring to FIGS. 1 and 2, there is shown a preferred embodiment of a blood pressure cuff formed in accordance with this invention. The cuff is formed from a sheet preform 2 which is shown in cross section in FIG. 2. The sheet 2 has a fabric component 4 preferably formed from nylon, and a polymeric coating 6 on one side of the fabric component 4 which coating is preferably polyurethane. As seen in FIG. 1, the nylon fabric 4 is face up, and the polyurethane coated surface 6 is face down. The sheet 2 is rectangular, and has a medial fold line 8 (shown in phantom) which traverses the longer dimension of the sheet 2. The fold line 8 divides the sheet 2 into two opposite halves. Openings 10 and 12 are die cut in one half of the sheet, and an opening 14 is die cut in the other half of the sheet 2 diagonally opposite the openings 10 and 12. Small openings 16 and 17 are cut in the sheet 2 at the fold line 8 in the general area of the openings 10 and 12. The openings 16 and 17 are separated by an intervening web 15.

Two loop fastener components 18 and 20 are adhered to a nylon/urethane coated patch 22. As viewed in FIG. 1, the patch 22 has its polyurethane coated surface 23 facing upward so as to face the polyurethane coated surface 6 of the sheet preform 2. The patch 22 is adhered to the sheet preform 2 to close the openings 10 and 12 by bringing the polyurethane coated surface 23 on the patch 22 against the polyurethane coated surface 6 on the preform 2, and then heat fusing the patch 22 to the preform 2. The loop components 18 and 20 are each provided with fusable polymer coated backing surfaces 21 and 26 respectively. These surfaces 21 and 26 are brought into abutting contact with the coated surface 23 on the patch 22, and the components 18 and 20 are then fused to the patch 22 which at this time has sealed openings 10 and 12. The loop components 18 and 20 are thus secured in place for use on the cuff. When the preform 2 is folded about the fold line 8, the opening 14 is brought into registry with the polyurethane coated surface 6 of the preform 2. The hook component 30, as seen in FIG. 1, has its hook surface 32 facing downwardly, and has its fusable polymer coated surface 34 facing upwardly, toward the polymer coated surface 6 of the preform 2. In assembling the cuff, the hook component 30 has its coated surface 34 pressed against the preform coated surface 6 through the opening 14, and is then heat fused to the preform surface 6. The hook component 30 is thus secured to the cuff, opposite the loop components 18 and 20. The dimensions of the hook component 30 equal, or are slightly smaller than the those of the opening 14 so that the hook component 30 covers the opening 14. An inflation hose fitting 36 formed from polyurethane, and having a radial flange 38 and two tubular projections 37 adapted to be connected to instrument inflation and sensor hoses is inserted from the coated side 6 of the sheet 2 so as to project through the openings 16 and 17, with the flange 38 abutting the side 6 of the sheet 2. The flange 38 is then fused to the side 6 of the sheet 2.

Figure 3:
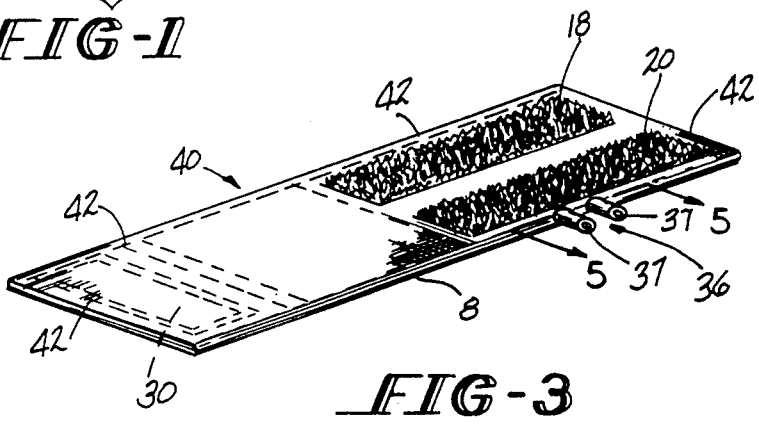
FIG. 3 is a perspective view of the cuff after the preform of FIG. 1 has been folded and sealed.

Referring to FIG. 3, details of the assembled cuff 40 are shown. It will be noted that the loop components 18 and 20 are accessible on one side of the cuff 40, and the hook component 30 is accessible on the opposite side of the other end of the cuff 40. The edges of the cuff 40, at 42, are sealed together to form an internal inflatable chamber 44, with which chamber the fitting 36 and tubes 37 communicate. It will be noted that the fold 8 forms one edge of the chamber 44.

Figure 4:
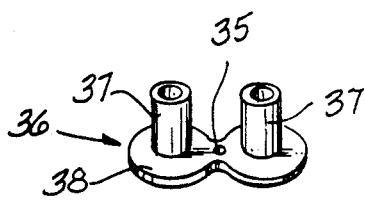
FIG. 4 is a perspective view of the fitting component used to form the cuff.

FIG. 4 shows details of the fitting 36. It will be noted that the flange 38 extends around and between both tubes 37, and an opening 35 is formed in the flange between the tubes 37 to weaken the flange so that it can be easily ruptured to separate the two tubes and, in effect, form two identical separate tubular fittings for use in a cuff which only uses one tube. It will be noted, however, that the opening 35 does not interfere with the ability of the flange 38 to provide a sealing surface around both of the tubes 37 as will be seen in FIG. 5.

Figure 5:
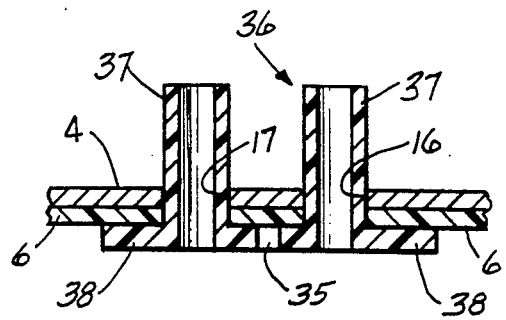
FIG. 5 is sectional view of the cuff taken along line 5—5 of FIG. 3.

Viewing FIG. 5, it will be noted that the flange 38 is pressed tightly against the coating 6, and that the opening 35 is smaller than the distance between the holes 16 and 17 through which tubes 37 project. The tubes also contact the edges of the coating 6 formed by the holes 16 and 17. The fitting 36 thus completely surrounds both of the holes 16 and 17, and thus can seal the latter against air leaks when fused to the coating 6.

It will be readily appreciated that the cuff of this invention is of simple construction, easy to assemble and relible. The inflation chamber is not compromised by the securement of the fitting to the cuff. The particular polymers used for the coatings and fitting are selected for their ability to seal the cuff against air permiability, and should be heat fusable. Polyurethane is preferred, but is by no means, the only polymer that can be used for these components. The fitting can be used in dual or single hose cuffs. The fitting modification necessary to be used with a single hose cuff, i.e., splitting the dual hose component, can be performed at the assembly table.

Since many changes and variations of the disclosed embodiment of the invention may be made without departing from the inventive concept, it is not intended to limit the invention otherwise than as required by the appended claims.

What is claimed is:

1. An inflatable blood pressure cuff formed from a woven fabric sheet having one surface thereof coated with a fusable polymer to render the fabric impermeable to air, said coated surface forming the interior of the cuff, and said sheet being folded about a medial fold line to bring said coated surface into contact with itself, said cuff including an inflatable chamber bounded by said medial fold line and by edges of said coated surface which are fused together; and a one piece molded air hose fitting formed from said fusable polymer, said fitting comprising a pair of adjacent tubular hose connections, and a basal flange completely surrounding both of said hose connections, said flange being fused to said said polymer coating in said inflatable chamber, with said hose connections projecting through adjacent openings in said sheet to access said chamber to external inflation/deflation and pulse sensing hoses.

2. The blood pressure cuff of claim 1 wherein said adjacent openings are disposed on said medial fold line.

3. The blood pressure cuff of claim 2 wherein said basal flange includes an opening therein midway between said tubular connections operable to weaken said flange whereby said tubular connections can be separated into two identical fittings each having one tubular connection and a basal flange.

4. A blood pressure cuff fitting for connecting a blood pressure cuff to a pair of hoses, said fitting being formed from a molded fusable polymer and including a pair of adjacent tubular hose connections and a basal flange integral with and completely surrounding both of said hose connections, said flange having an opening formed therein midway between said hose connections, said opening weakening said flange sufficiently to allow said fitting to be easily separated into two like fittings, each with a hose connection and a basal flange.

* * * * *